United States Patent [19]

Bellus et al.

[11] 4,440,694
[45] Apr. 3, 1984

[54] PROCESS FOR THE PRODUCTION OF VINYLSTILBENE COMPOUNDS

[75] Inventors: Daniel Bellus, Riehen; Hans-Ulrich Blaser, Ettingen; Guglielmo Kabas, Aesch, all of Switzerland; Dieter Reinehr, Kandern, Fed. Rep. of Germany; Alwyn Spencer; Kurt Weber, both of Basel, Switzerland

[73] Assignee: Ciba-Geigy Corporation, Ardsley, N.Y.

[21] Appl. No.: 262,001

[22] Filed: May 8, 1981

[30] Foreign Application Priority Data

May 13, 1980 [CH] Switzerland ............... 3730/80
Mar. 5, 1981 [CH] Switzerland ............... 1474/81

[51] Int. Cl.³ ............... C07C 121/70; C07C 69/618; C07C 103/24
[52] U.S. Cl. ............... 260/465 D; 260/465 H; 560/8; 560/81; 564/156; 568/316; 585/437; 549/398; 549/499
[58] Field of Search ......... 260/465 D, 465 H, 465 K; 560/8, 81; 568/316; 542/447; 564/156; 585/437

[56] References Cited

U.S. PATENT DOCUMENTS 3,527,794 9/1970 Fleck ................... 260/465 D X
3,803,175 4/1974 Sparks et al. ........... 260/343.2 R
3,922,299 11/1975 Fleck ..................... 560/104
4,108,887 8/1978 Fleck et al. ............. 260/465 H

FOREIGN PATENT DOCUMENTS 2059291 6/1972 Fed. Rep. of Germany .

OTHER PUBLICATIONS

Chiusoli et al., Transition Met. Chem., vol. 2, pp. 270-272 (1977).
Biavati et al., Transition Met. Chem., vol. 4, pp. 398-399 (1979).
Tohda et al., Synthesis, Nov. 1977, pp. 777-778 (1977).
Biavati et al., "Palladium or Nickel-Catalyzed Benzoylation and Phenylation of Methyl Acrylate," Transition Met. Chem. 4, 398-399 (1979).

*Primary Examiner*—Dolph H. Torrence
*Attorney, Agent, or Firm*—Edward McC. Roberts

[57] ABSTRACT

The invention relates to vinylstilbene compounds of the formula

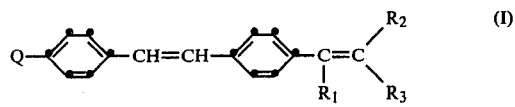 (I)

wherein Q is the grouping —COX or

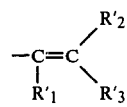

These compounds are obtained by reacting 1 molar equivalent of a compound of the formula II

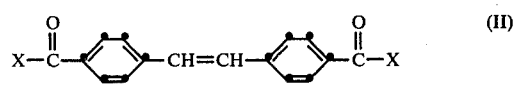 (II)

wherein X is chlorine, bromine or iodine, in the presence of a base and with the addition of palladium metal or of palladium compounds, as catalyst, which, under the reaction conditions, form labile palladium(O) compounds which do not contain phosphorus, with 1 molar equivalent of a compound of the formula III or with 1 molar equivalent of each of the compounds of the formulae III and IV (III) 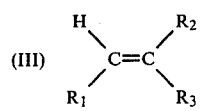 (IV)

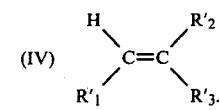

13 Claims, No Drawings

PROCESS FOR THE PRODUCTION OF VINYLSTILBENE COMPOUNDS

The present invention relates to a novel process for the production of vinylstilbene compounds, to the novel vinylstilbene compounds obtained by said process, and to the use of these compounds for whitening organic materials.

The use of such vinylstilbene compounds as fluorescent whitening agents and different methods of obtaining them are disclosed in U.S. Pat. No. 4,108,887. From U.S. Pat. No. 3,922,299 it is known that vinylically or allylically substituted organic compounds, especially cinnamic acid and cinnamates, can be obtained by the catalytic reaction of corresponding halides with activated olefins such as methyl acrylate, in the presence of tertiary amines. As catalysts it is preferred to use mixtures of palladium acetate and triphenylphosphine or tri(orthotolyl)phosphine.

The reaction can also be carried out by first forming a complex from the halide and the catalyst system and then reacting this complex, in the presence of a tertiary amine, with the olefin. It is known, however, that the reaction of benzoyl chloride with methyl acrylate in the presence of stoichiometric amounts of a nickel(O) catalyst results in the formation of trans-3-benzoylacrylic acid methyl ester on subsequently treating the reaction mixture with iodine in methanol, with methyl cinnamate being obtained as by-product. Reaction of a complex consisting of benzoylpalladium chloride and triphenylphosphine with methyl acrylate at 70°–85° C., in the presence of triethylamine, results in methyl cinnamate being obtained as main product and methyl benzoylacrylate as by-product. If only catalytic amounts of palladium and triphenylphosphine are used, then there is a shift in the equilibrium of the reaction to promote the formation of methyl benzoylacrylate (weight ratio of methyl benzoylacrylate to methyl cinnamate=c. 8.3:1) [q.v. Transition Met. Chem., 2, 270 (1977) and 4, 398 (1979)]. Finally, it is known from Synthesis, 777 (1977) that aromatic acid halides can be reacted with alkines, under palladium catalysis, to give alkynyl ketones, without decarbonylation.

It has now been found that vinylstilbene compounds of the formula

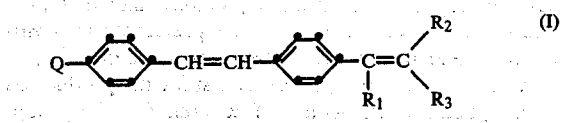

wherein Q is the grouping —COX or

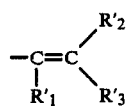

and each of $R_1$ and $R_1'$ independently is hydrogen, cyano, alkyl or a non-chromophoric esterified carboxyl group, each of $R_2$ and $R_2'$ independently is hydrogen, alkyl or alkenyl each unsubstituted or substituted by non-chromophoric substituents, or is a non-chromophoric second order substituent, each of $R_3$ and $R_3'$ independently is hydrogen, cyano, or alkyl or alkenyl each unsubstituted or substituted by non-chromophoric substituents, and X is chlorine, bromine or iodine, or $R_1$ together with $R_3$ or $R_1'$ together with $R_3'$ are an alkylene bridge, with the proviso that not more than one of $R_2$ and $R_3$ and not more than one of $R_2'$ and $R_3'$ are hydrogen, and that, if Q is —COX, $R_1$ and $R_3$ are hydrogen and $R_2$ is carboxylic acid ($C_1$–$C_4$)alkyl ester or cyano, can be obtained by reacting 1 molar equivalent of a compound of the formula II

wherein X is as defined above, in the presence of a base and with the addition, as catalyst, of palladium compounds which, under the reaction conditions, form labile palladium(O) compounds which do not contain phosphorus, with 1 molar equivalent of a compound of the formula III or with 1 molar equivalent of each of the compounds of the formulae III and IV

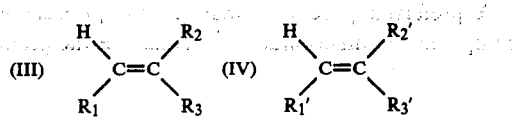

wherein $R_1$, $R_2$ and $R_3$ and $R_1'$, $R_2'$ and $R_3'$ are as defined above.

The compounds of the formula I can be obtained by the process of this invention economically and using readily obtainable starting compounds. Moreover, it is surprising that the reaction proceeds selectively with decarbonylation of the acid halides of the formula II.

The substituents in the compounds of the formula I are in general those common in the field of fluorescent whitening agents.

Alkyl groups $R_1$, $R_1'$, $R_2$, $R_2'$, $R_3$ and $R_3'$ can be straight-chain or branched and contain preferably 1 to 6, most preferably 1 or 2, carbon atoms. Alkenyl groups $R_2$, $R_2'$, $R_3$ and $R_3'$ contain preferably 2 to 4, most preferably 3, carbon atoms. Representative examples of such alkyl and alkenyl groups are: methyl, ethyl, n-propyl, isopropyl, n-butyl, tert-butyl, n-pentyl, n-hexyl, vinyl and allyl.

Examples of suitable non-chromophoric substituents of alkyl or alkenyl groups are alkoxy, alkoxyalkoxy, dialkylamino or alkoxycarbonyl groups, and also halogen atoms such as fluorine or chlorine atoms, or phenyl which is unsubstituted or substituted by non-chromophoric groups, e.g. phenyl optionally substituted by alkyl, alkoxy, halogen, cyano, a carboxylic acid ester or carboxamide group, or by a carboxylic acid acyl radical. Alkoxy or alkyl moieties of the above substituents preferably contain 1 to 4, most preferably 1 or 2, carbon atoms. Alkenyl groups $R_2$, $R_2'$, $R_3$ and $R_3'$ are preferably unsubstituted. Alkoxyalkoxy substituents preferably contain 2 to 6, most preferably 4 to 6, carbon atoms. Alkylene bridge members in alkoxyalkoxy substituents are preferably ethylene, 1,2-propylene, 1,2-butylene or 2,3-butylene, with ethylene being preferred.

Alkylene represented by $R_1$ and $R_3$ together and by $R_1'$ and $R_3'$ together is e.g. 1,3-propylene or 1,4-butylene.

Second order non-chromophoric substituents are electrophilic substituents which do not impart colour to the compounds of the formula I, thereby making them unsuitable for use as fluorescent whitening agents. Representative examples of such substituents are: acyl radicals of organic non-chromophoric carboxylic acids, the cyano and trifluoromethyl group, unsubstituted or substituted phenylalkyl, carboxylic acid and carboxamide groups. The ester groups present in the molecule, especially the non-chromophoric esterified carboxyl groups, are e.g. unsubstituted or alkylsubstituted carboxylic acid cycloalkyl ester groups or carboxylic acid alkyl ester groups, the alkyl moiety of which can be substituted by alkoxy or alkoxyalkoxy groups of the kind specified above; and also unsubstituted or substituted carboxylic acid phenyl ester or phenylalkyl ester groups, the phenyl moiety of which can be substituted as indicated above.

Carboxamide groups can be substituted or preferably unsubstituted. Examples of suitable substituents are alkyl, alkoxyalkyl, dialkylaminoalkyl, cycloalkyl, and unsubstituted or substituted phenyl or phenylalkyl groups.

A preferred process is that for the production of compounds of the formula I, wherein Q is the grouping

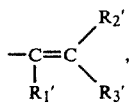

and wherein each of $R_1$ and $R_1'$ independently is hydrogen, —CN, $C_1$–$C_6$alkyl or —COOR''', preferably hydrogen, —CN or $C_1$–$C_4$alkyl and, most preferably, hydrogen or methyl; each of $R_2$ and $R_2'$ independently is hydrogen or $C_1$–$C_6$alkyl unsubstituted or substituted by $C_1$–$C_4$alkoxy or $C_2$–$C_5$alkoxycarbonyl, or is $C_2$–$C_4$alkenyl, —CN, —CF$_3$ or a group

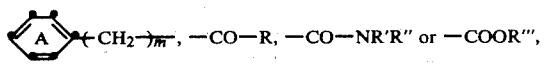

preferably $C_2$–$C_4$alkenyl and, most preferably, —CN, —CONR'R'', —COOR''' or —CO—R, especially —CN or —COOR'''; and each of $R_3$ and $R_3'$ independently is hydrogen, —CN, or $C_1$–$C_6$alkyl unsubstituted or substituted by $C_1$–$C_4$alkoxy or $C_2$–$C_5$alkoxycarbonyl, preferably hydrogen, —CN or $C_1$–$C_4$alkyl, preferably methyl and most preferably hydrogen; or $R_1$ and $R_3$ and $R_1'$ and $R_3'$ together and —(CH$_2$)$_3$ or —(CH$_2$)$_4$, with the proviso that not more than one of $R_2$ and $R_3$ and not more than one of $R_2'$ and $R_3'$ are hydrogen; R is methyl, $C_2$–$C_6$alkyl unsubstituted or substituted by $C_1$–$C_4$alkoxy or $C_4$–$C_6$alkoxyalkoxy, a radical of the formula

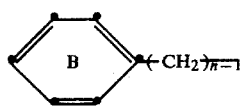

or naphthyl, especially methyl, $C_2$–$C_6$alkyl unsubstituted or substituted by $C_1$–$C_4$alkoxy or $C_4$–$C_6$alkoxyalkoxy, the radical of the formula

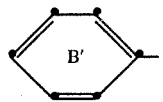

or naphthyl and, most preferably, phenyl unsubstituted or substituted by chlorine, methyl or methoxy, unsubstituted $C_1$–$C_6$alkyl, preferably $C_1$–$C_4$alkyl and most preferably methyl; R' is hydrogen, methyl, $C_2$–$C_6$alkyl unsubstituted or substituted by $C_1$–$C_4$alkoxy, $C_4$–$C_6$alkoxyalkoxy or di($C_1$–$C_4$alkyl)amino, unsubstituted or methyl- or ethyl-substituted cyclohexyl or a radical of the formula

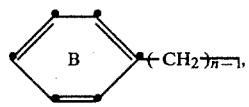

especially methyl; R'' is hydrogen, methyl or $C_2$–$C_6$alkyl unsubstituted or substituted by $C_1$–$C_4$alkoxy or $C_4$–$C_6$alkoxyalkoxy, especially methyl; R''' is methyl, $C_2$–$C_6$alkyl unsubstituted or substituted by $C_1$–$C_4$alkoxy or $C_3$–$C_6$alkoxyalkoxy, unsubstituted or methyl- and/or ethyl-substituted cyclohexyl or a radical of the formula

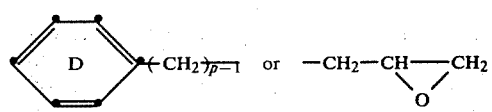

and, in particular, methyl or $C_2$–$C_6$alkyl unsubstituted or substituted by $C_1$–$C_4$alkoxy or $C_3$–$C_6$alkoxyalkoxy, especially $C_1$–$C_6$alkyl, preferably $C_1$–$C_4$alkyl, and, most preferably, methyl or ethyl; m is 1 or 2, preferably 1, each of n and p independently is 1, 2 or 3, preferably 2 and most preferably 1.

In the above formulae the aromatic rings A, B, C and D can be mono- or disubstituted by $C_1$–$C_3$alkyl and/or halogen, especially chlorine. If each of n and p is 1, the aromatic rings B and D can be trisubstituted by $C_1$–$C_3$alkyl and/or halogen, or they can be mono- or disubstituted by $C_1$–$C_3$alkoxy. The ring B' can be substituted by halogen, especially chlorine, $C_1$–$C_3$alkyl and/or $C_1$–$C_3$alkoxy. However, these rings are preferably unsubstituted. R' and R'' preferably have the same meaning.

A further preferred process is that for the production of compounds of the formula I, wherein Q is the grouping

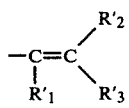

and wherein each of $R_1$ and $R_1'$ and $R_3$ and $R_3'$ is hydrogen, —CN or $C_1$–$C_4$alkyl, each of $R_2$ and $R_2'$ is $C_2$–$C_4$alkenyl, —CN, —CONR'R'', —COOR''' or —CO—R, whilst not more than one of $R_2$ and $R_3$ and not more than one of $R_1'$ and $R_3'$ are hydrogen and R, R', R'' and R''' are as defined above. The preferred identity of R is $C_1$–$C_6$alkyl or phenyl unsubstituted or substituted by halogen, especially chlorine, or by $C_1$–$C_3$alkyl or $C_1$–$C_3$alkoxy, or is, in particular, unsubstituted $C_1$–$C_4$alkyl or phenyl unsubstituted or monosubstituted by chlorine, methyl or methoxy. Each of R' and R" is preferably methyl.

R'" is preferably methyl or $C_2-C_6$alkyl unsubstituted or substituted by $C_1-C_4$alkoxy or $C_3-C_6$alkoxyalkoxy, with unsubstituted $C_1-C_4$alkyl being the most preferred identity.

The most preferred process is that for the production of compounds of the formula I, wherein Q is the grouping

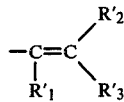

and wherein each of $R_1$ and $R_1'$ is methyl and, in particular, hydrogen, each of $R_2$ and $R_2'$ is —CN or —COOR'", R'" is unsubstituted alkyl of 1 to 4 carbon atoms and each of $R_3$ and $R_3'$ is methyl or ethyl and, in particular, hydrogen.

The compounds of the formulae II, III and IV are known or they can be obtained by methods which are known per se. As regards the production of compounds of the formula IV, attention is drawn to Houben-Weyl, Vol. 5/1b (1972).

As defined herein, the compounds of the formula II and IV are used in stoichiometric amount. However, it is preferred to use an excess of olefin of the formula IV, e.g. about 1.5 moles of olefin per acid halide group.

X in formula II is preferably chlorine.

The palladium compounds used in the process of this invention can be—in addition to palladium metal—e.g. compounds of the formula V $$M^y[PdL_n]^x \quad (V)$$

wherein n is an integer from 2 to 4, x is $2^+$ to $2^-$, y is $-(x)$, M is a counterion if x is not 0, and the Ls are identical or different ligands, e.g. Cl, Br, I, —CN, $-NO_3$, $C_1-C_{12}$alkyl—COO,

$NH_3$, 2,2'-bipyridyl, o-phenanthroline,

or —NC-phenyl. Examples of suitable compounds of the formula V are: $PdCl_2$, $PdBr_2$, $Pd(CN)_2$, $Pd(NO_3)_2$, $Pd(O_2C-C_{12}alkyl)_2$, especially $Pd(OOCCH_3)_2$,

$[Pd(NH_3)_4]$, $[PdCl_4]Na_2$, $Pd(OOCCH_3)_2(2,2'$-bipyridyl), $Pd(OOCCH_3)_2$(o-phenanthroline),

and $PdCl_2(NC-phenyl)_2$.

In addition to the above compounds, it is also possible to use palladium compounds of other stages of oxidation, e.g. bis-(dibenzylidene-acetone)palladium(O) and bis-(isonitrile)palladium(O) compounds. Representative examples of such isonitriles are: bis-(cyclohexylisonitrile)palladium(O), bis-(isopropylisonitrile)palladium(O), bis-(tert-butylisonitrile)palladium(O), bis-(p-tolylisonitrile)palladium(O), bis-(phenylisonitrile)palladium(O) and bis-(p-methoxyphenylisonitrile)palladium(O). Of these, preferred compounds are: bis-(dibenzylidene-acetone)palladium(O), bis-(cyclohexylisonitrile)palladium(O) and bis-(isopropylisonitrile)palladium(O).

The preferred catalysts are: $PdCl_2$, $PdBr_2$, $Pd(OOCCH_3)_2$,

$Pd(OOCCH_3)_2(2,2'$-bipyridyl), $PdCl_2(NC$-phenyl$)_2$, bis-(dibenzylidene-acetone)palladium(O) and bis-(cyclohexylisonitrile)palladium(O). The most preferred catalysts are: $PdCl_2$, palladium acetate and bis-(dibenzylidene-acetone)palladium(O).

It is preferred to use in general 0.0001 to 20 mol.% of catalyst, most preferably 0.001 to 3 mol.%, based on the compound of the formula II.

As bases for the process of the invention it is possible to use both organic and inorganic compounds which are sufficiently soluble in the reaction medium. Examples of suitable bases are compounds of the formulae VI to VIII

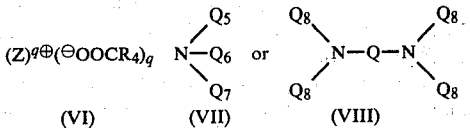

as well as cyclic tertiary amines, e.g. N-methyl- or N-ethylpiperidine, 1,2,2,6,6-pentamethylpiperidine, 4-oxo-1,2,2,6,6-pentamethylpiperidine, 1,4-diazabicyclo[2,2,2]octane (DABCO), N-alkylmorpholines and N-alkylpyrrolidines such as N-methyl- and N-ethylmorpholine, N-methyl- and N-ethylpyrrolidine, or N,N'-dialkylpiperazines such as N,N'-dimethylpiperazine.

In the formulae (VI), (VII) and (VIII) above, q is 1 or 2, $R_4$ is phenyl or $C_1-C_{17}$alkyl, Z is an alkali metal cation, an alkaline earth metal cation or

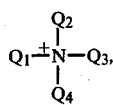

Q is straight-chain or branched alkylene of 2 to 6 carbon atoms, $Q_1$ is hydrogen, $C_1-C_{12}$alkyl, cyclopentyl, cyclohexyl, benzyl or phenyl, $Q_2$, $Q_3$ and $Q_4$ are identical or different $C_1-C_{12}$alkyl groups, $Q_5$ is $C_1-C_{12}$alkyl, cyclopentyl, cyclohexyl, phenyl, benzyl, or benzyl substituted by a halogen atom such as chlorine or bromine, or by an alkyl or alkoxy group of 1 to 4, especially 1 or 2, carbon atoms, $Q_6$ and $Q_7$ are identical or different $C_1-C_{12}$alkyl groups, and $Q_8$ is methyl or ethyl.

Z as an alkali metal cation is preferably the sodium and, most preferably, the lithium cation. Alkyl groups $R_4$ and $Q_1$ and $Q_7$ can be straight-chain or branched. Alkyl groups $Q_5$ and $Q_7$ preferably each contain at least 4 carbon atoms, whereas alkyl groups $Q_1$ to $Q_4$ each contain 1 to 4 carbon atoms. Examples of compounds of the formulae VI to VIII are: lithium acetate, lithium butyrate, lithium stearate, barium and calcium acetate, potassium, calcium or sodium stearate, lithium and sodium benzoate, as well as the corresponding trimethyl-, tetramethyl-, tetraethyl- and tetra-n-butylammonium salts; triethylamine, tri-n-butylamine, tri-(2-ethylhexylamine), tri-n-octylamine and tri-n-dodecylamine; N,N-benzyldialkylamines such as N,N-benzyldimethylamine, N,N-benzyldiethylamine, N,N-(4-chlorobenzyl)-dimethylamine and N,N-(3-methyl- or 3-methoxybenzyl)dimethylamine, N,N,N',N'-tetramethyl- and N,N,N',N'-tetraethylethylenediamine, N,N,N',N'-tetramethyl-1,3-diaminopropane and N,N,N',N'-tetramethyl-1,6-diaminohexane.

The preferred bases are compounds of the formula VII, wherein $Q_5$ is 4-chlorobenzyl, 3-methyl- or 3-methoxybenzyl and, in particular, benzyl, and each of $Q_6$ and $Q_7$ is alkyl of 1 to 4, preferably 1 or 2, carbon atoms, or wherein each of $Q_5$, $Q_6$ and $Q_7$ is alkyl of 3 to 12 carbon atoms. Particularly preferred bases are N-benzyldimethylamine, N-ethylmorpholine and tri-n-butylamine.

The reaction temperature for the process of this invention is advantageously in the range from 0° to 200° C., preferably from 90° to 150° C. If the acid halides of the formula II are liquid, then the reaction can be carried out without the addition of a solvent. In general, however, the reaction is conducted in an inert organic solvent. Examples of suitable inert organic solvents are unsubstituted or chlorinated aliphatic or aromatic hydrocarbons such as n-pentane, n-heptane, n-octane, benzene, toluene, xylenes and chlorobenzenes; aromatic, aliphatic and cyclic ethers such as anisole, diethyl ether, diisopropyl ether, tetrahydrofurane and dioxane; nitriles, especially benzonitrile and alkylnitriles containing 2 to 5 carbon atoms such as acetonitrile, propionitrile and butyronitrile; 3-methoxypropionitrile and 3-ethoxypropionitrile; tertiary alcohols containing 4 to 8 carbon atoms, especially tert-butanol; aliphatic and cycloaliphatic ketones such as acetone, diethyl ketone, methyl isopropyl ketone, cyclopentanone and cyclohexanone; esters such as esters of carbonic acid, e.g. diethyl carbonate, and alkyl and alkoxyalkyl esters of aliphatic monocarboxylic acids containing a total of 2 to 8 carbon atoms, such as methyl acetate, ethyl acetate, n-butyl acetate and isobutyl acetate, ethyl butyrate and n-butyl butyrate, as well as 1-acetoxy-2-methoxyethane. Preferred solvents are nitriles, ketones, esters, cyclic ethers and aromatic hydrocarbons of the kind specified above.

Polar solvents such as nitriles, ketones and esters are especially suitable for the reaction in the presence of inorganic bases. It is most preferred to conduct the reaction in the presence of an organic base and of an aromatic ether or hydrocarbon, in particular anisole, xylenes or toluene.

The reaction course can be easily followed from the evolution of CO, for example using a bubble counter. In the case of reaction products which are of only limited solubility in the reaction mixture it is advisable to discontinue the reaction when the evolution of CO is complete and to work up the reaction product direct.

The compounds of the formula I can be isolated in a manner known per se and, if desired or necessary, purified. As mentioned at the outset, they are fluorescent whitening agents which are known per se and whose fields of use and formulations are described in U.S. Pat. No. 4,108,887.

In a further aspect, the present invention relates to novel vinylstilbene compounds of the formula

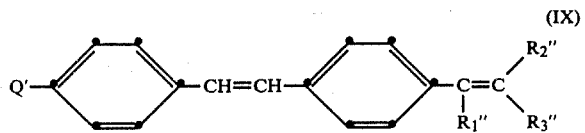

wherein Q' is —COCl or

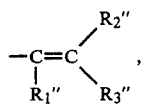

and if Q is —COCl, $R_1''$ and $R_3''$ are hydrogen and $R_2''$ is —COOCH$_3$, —COOC$_2$H$_5$ or —CN, and, if Q' is

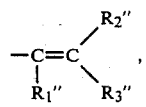

$R_1''$ and $R_3''$ are cyano and $R_2''$ is

—(CH$_2$)$_2$CN, —COC$_2$H$_5$, —COO(CH$_2$)$_2$CN,

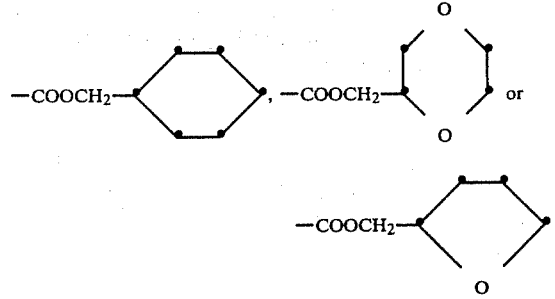

The compounds of the formula (IX), wherein Q is —COCl, are intermediates for obtaining known fluorescent whitening agents, e.g. those of U.S. Pat. No. 4,108,887.

The compounds of the formula (IX), wherein Q' is

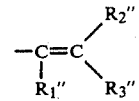

exhibit a more or less pronounced fluorescence in the dissolved or finely divided state. They are therefore used in the practice of this invention for whitening and/or brightening a wide variety of synthetic, regenerated man-made or natural organic materials in the textile industry.

Without any restriction being implied by the following classification, representative examples of textile fibres obtained from the following groups of organic materials which can be treated with fluorescent whitening agents, are:

I. Man-made organic material of high molecular weight:

(a) polymerisation products based on organic compounds containing at least one polymerisable carbon-carbon double bond, that is to say their homopolymers of copolymers as well as their aftertreatment products, for example, crosslinking, grafting or degradation products, polymer blends, or products obtained by modification of reactive groups, for example polymers based on $\alpha,\beta$-unsaturated carboxylic acids or derivatives of such carboxylic acids, especially on acrylic compounds, for example acrylates, acrylic acid, acrylonitrile, acrylamides and their methacrylic analogues, on olefin hydrocarbons (for example ethylene, propylene, styrenes or dienes and also ABS polymers), and polymers based on vinyl and vinylidene compounds (for example vinyl chloride, vinyl alcohol and vinylidene chloride);

(b) polymerisation products which can be obtained by ring opening, for example, polyamides of the polycaprolactam type, and also polymers which are obtained both by polyaddition and by polycondensation, for example polyethers or polyacetals;

(c) polycondensation products or precondensates based on bifunctional or polyfunctional compounds with condensable groups, their homocondensation and co-condensation products, and also aftertreatment products, for example polyesters, especially saturated polyesters (for example ethylene glycol terephthalic acid polyesters) or unsaturated polyesters (for example maleic acid-dialcohol polycondensates as well as their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, their precondensates and analogues, polycarbonates or silicones;

(d) polyadducts such as polyurethanes (crosslinked and uncrosslinked) or epoxy resins.

II. Regenerated man-made organic material, for example, cellulose esters of varying degrees of esterification (cellulose 2 ½-acetate or triacetate) or cellulose ethers, regenerated cellulose (viscose or cuprammonium cellulose), or their aftertreatment products, and also casein plastics.

III. Natural organic textiles of animal or vegetable origin, for example based on cellulose or proteins, e.g. cotton, wool, linen, or silk. Fibrous material can be, for example, in the form of staple fibres, flocks, hanks, textile filaments, yarns threads, nonwovens, felts, waddings, flocked structures, woven textile or bonded textile fabrics, or knitted fabrics.

The compounds defined above are of particular importance for the treatment of organic woven textile fabrics. The treatment of textile substrates is advantageously effected in an aqueous medium in which the fluorescent whitening agents are finely dispersed (suspensions, microdispersions, or, optionally, solutions). If necessary or desirable, dispersing agents, stabilisers, wetting agents and further assistants can be added during the treatment.

Depending on the type of fluorescent whitening agent used, it can be advantageous to carry out the treatment in a neutral, alkaline, or acid bath. The treatment is usually carried out in the temperature range from 20° to 140° C., for example at the boiling point of the bath or near it (about 90° C.). Solutions or emulsions in organic solvents are also suitable for finishing textile substrates in accordance with this invention, as is practised in the dyeing industry in so-called solvent dyeing (pad-thermofixation application, or exhaust dyeing methods in dyeing machines).

The fluorescent whitening agents of the present invention can also be employed e.g. in the following formulations:

(a) in mixtures with dyes (shading) or pigments (coloured pigments or especially, for example, white pigments), or as an additive to dyebaths, printing pastes, discharge pastes or reserve pastes, as well as for the aftertreatment of dyeings, prints or discharge prints;

(b) in mixtures with carriers, wetting agents, plasticisers, swelling agents, antioxidants, light stabilisers, heat stabilisers, and chemical bleaching agents (chlorite bleach or bleaching bath additives);

(c) in admixture with crosslinking agents or finishing agents (for example starch or synthetic finishes), and in combination with a wide variety of textile finishing processes, especially synthetic resin finishes (for example creaseproof finishes such as wash-and-wear, permanent-press or non-iron), as well as flameproof finishes, soft finishes, antisoiling or antistatic finishes, or microbicidal finishes;

(d) incorporation of the fluorescent whitening agent in polymer carriers (polymerisation, polycondensation or polyaddition products, in dissolved or dispersed form, for use e.g. in coating agents, impregnating agents or binders (solutions, dispersions and emulsions) for textiles, non-wovens etc.;

(e) as additives to master batches;

(f) as additives to soaps and detergents;

(g) in combination with other fluorescent whitening agents.

If the whitening process is combined with textile treatment or finishing methods, the combined treatment can in many cases advantageously be carried out with the aid of appropriate stable preparations which contain the fluorescent whitener compounds in a concentration such that the desired white effect is achieved.

In certain cases the fluorescent whitening agents are made fully effective by an aftertreatment. This can be, for example, a chemical treatment (for example acid treatment), a thermal treatment or a combined chemical/thermal treatment. Thus, for example, the appropriate procedure to follow in whitening a number of fibre substrates, for example polyester fibres, with the fluorescent whitening agents of the present invention, is to impregnate these fibres with the aqueous dispersions (or optionally also solutions) of the whitening agents at temperatures below 75° C., for example at room temperature, and to subject them to a dry heat treatment at temperatures above 100° C., it being generally advisable additionally to dry the fibrous material beforehand at moderately elevated temperature, for example in the range from at least 60° to about 130° C. The heat treatment in the dry state is then advantageously carried out in the temperature range from 120° to 225° C., for example by heating in a drying chamber, by ironing within the specified temperature range or by treatment with dry, superheated steam. The drying and dry heat treatment can also be carried out in immediate succession or be combined in a single procedure.

The amount of fluorescent whitening agent of the present invention to be used, based on the weight of the material to be whitened, can vary within wide limits. A marked and lasting effect can be obtained even with very insignaficant amounts, in certain cases 0.0001 percent by weight. But it is also possible to use amounts of up to 0.8 percent by weight and, on occasion, up to about 2 percent by weight. For most practical purposes, it is preferred to use amounts between 0.0005 and 0.5 percent by weight.

The fluorescent whitening agents of this invention are also particularly suitable for use as additives for wash liquors or heavy duty and domestic detergents, to which they can be added in various ways. They are advantageously added to wash liquors in the form of their solutions in water or organic solvents, or, in dispersed form, as aqueous dispersions. They are advantageously added to detergents in any stage of the production of the latter, for example to the slurry before the washing powder is atomised, or during the preparation of liquid detergent combinations. They can be added either in the form of a solution or dispersion in water or other solvents, or without assistants, as a dry powder. For example, the whitening agents can be mixed, kneaded or ground with the active detergent and, in this form, admixed with the finished washing-powder. However, they can also be sprayed in dissolved or predispersed form onto the finished detergent.

Suitable detergents are the known mixtures of active detergents, for example soap in the form of chips and powders, synthetics, soluble salts of sulfonic acid hemiesters of higher fatty alcohols, arylsulfonic acids with higher and/or multiple alkyl substituents, sulfocarboxylic acid esters of medium to higher alcohols, fatty acid acylaminoalkyl- or acylaminoaryl-glycerol sulfonates and phosphoric acid esters of fatty alcohols. Suitable builders which can be used are, for example, alkali metal polyphosphates and polymetaphosphates, alkali metal pyrophosphates, alkali metal salts of carboxymethyl cellulose and other soil redeposition inhibitors, and also alkali metal silicates, alkali metal carbonates, alkali metal borates, alkali metal perborates, nitrilotriacetic acid, ethylenediaminetetraacetic acid, and foam stabilisers such as alkanolamides of higher fatty acids. The detergents can further contain for example: antistatic agents, fat restorative skin protectives such as lanolin, enzymes, microbicides, perfumes, and colorants.

The novel fluorescent whitening agents have the particular advantage that they are also effective in the presence of active chlorine donors, for example, hypochlorite, and can be used without significant loss of effect in wash liquors containing non-ionic detergents, for example alkylphenolpolyglycol ethers.

Wash liquors which contain the indicated amounts of the fluorescent whitening agents to be used in the practice of this invention impart a brilliant appearance in daylight when used for washing textiles made from cellulose fibres, polyamide fibres, resin-finished cellulose fibres, polyester fibres or wool.

The washing treatment is carried out e.g. as follows: The textiles are treated for 1 to 30 minutes at 20° to 100° C. in a wash liquor which contains 1 to 10 g/kg of a built-up composite detergent and 0.05 to 1%, based on the weight of the detergent, of the fluorescent whitening agent. The liquor ratio can be 1:3 to 1:50. After they have been washed, the textiles are rinsed and dried in the usual manner. The wash liquor can contain 0.2 g/l of active chlorine (for example in the form of hpochlorite) or 0.1 to 2 g/l of sodium perborate.

In the following Examples, percentages are always by weight. Unless otherwise stated, melting and boiling points are uncorrected.

EXAMPLE 1

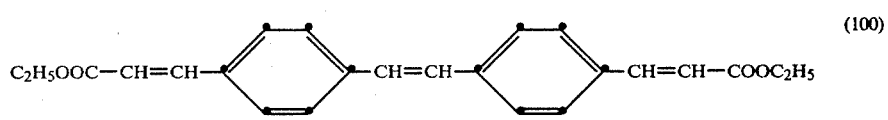

(100)

A 100 ml flask is charged with 6.1 g (0.02 mole) of stilbene-4,4'-dicarboxylic acid chloride [prepared in accordance with Fosdick and Urback, J. Am. Chem. Soc. 69, 503 (1947, Hager and Schonle, J. Am. Chem. Soc. 68, 2167 (1946) and J. Chem. Soc. 1024 (1948)], 5.2 g (0.05 mole) of ethyl acrylate, 5.06 g (0.05 mole) of triethylamine, 20 ml of toluene and 0.089 g (0.0004 mole) of palladium acetate, and the mixture is heated, with stirring, to 100° C. (bath temperature). Slight evolution of gas is observed. After the batch has been stirred for 6 hours, the reaction product is extracted with toluene and the combined extracts are evaporated to dryness and the residue is recrystallised from benzene, affording 3.4 g (45% of theory) of stilbene-4,4'-bisacrylic acid ethyl ester in the form of greenish yellow flakes with a melting point of 245°–248° C.

Analysis (mol. wt. 376.45): Calculated: C 76.57%; H 6.43%; O 17.00%. Found: C 76.82%; H 6.24%; O 17.03%.

EXAMPLE 2

The procedure of Example 1 is repeated, using 9.25 g (0.05 mole) of tri-n-butylamine. After working up as described in Example 1, stilbene-4,4'-bisacrylic acid ethyl ester is obtained in a yield of 56%.

The compounds of the formula

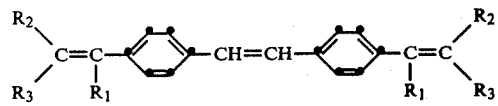

listed in the following table are obtained by repeating the above procedure, using the corresponding olefins.

| Compound | $R_1$ | $R_2$ | $R_3$ | melting point °C. |
|---|---|---|---|---|
| 101 | H | —COO—CH$_2$—(tetrahydrofurfuryl) | H | 152–154 |
| 102 | H | —COO(CH$_2$)$_2$—O(CH$_2$)$_3$—OCH$_3$ | H | 122–124 |

-continued

| Compound | R₁ | R₂ | R₃ | melting point °C. |
|---|---|---|---|---|
| 103 | H | −COO−CH₂−[dioxolane] | H | 180–181 |
| 104 | H | −COOCH₂−[cyclohexadiene] | H | 169–170 |
| 105 | CN | −(CH₂)₂−CN | H | 230–232 |
| 106 | H | CN | CN | >300 |
| 107 | H | −CO−C₂H₅ | H | 244–246 |
| 108 | H | −CON(C₂H₅)₂ | H | 210–211 |
| 109 | −COOCH₃ | −CH₂COOCH₃ | H | 157–158 |
| 110 | H | −COOCH₃ | H | 269–270 |
| 111 | H | −COO(CH₂)₂CN | H | 213–215 |

EXAMPLE 3

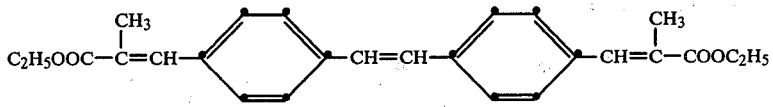

The procedure of Example 1 is repeated, using 8.7 g (0.05 mole) of ethyl methacrylate instead of ethyl acrylate. Working up gives stilbene-4,4'-bismethacrylic acid ethyl ester in the form of greenish yellow flakes with a melting point of 123°–125° C.

Analysis (mol. wt. 404): Calculated: C 77.17%; H 7.02%; O 15.81%. Found: C 77.27%; H 7.08%; O 15.65%.

EXAMPLE 4

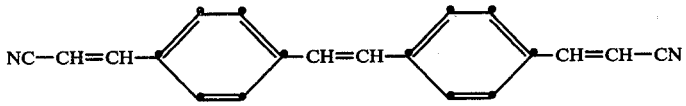

The procedure of Example 1 is repeated, using 2.65 g (0.05 mole) of acrylonitrile instead of ethyl acrylate. Working up gives stilbene-4,4'-bisacrylonitrile in the form of greenish yellow crystals with a melting point of 219°–221° C.

Analysis (mol. wt. 282): Calculated: C 85.08%; H 5.00%; N 9.92%. Found: C 84.75%; H 5.07%; N 9.67%.

EXAMPLE 5

The procedure of Example 1 is repeated, using 0.0112 g (0.00005 mole) of palladium acetate and 6.76 g (0.05 mole) of N-benzyldimethylamine. Yield: 1.54 g of compound (100).

EXAMPLE 6

The procedure of Example 1 is repeated, using 6.76 g (0.05 mole) of N-benzyldimethylamine. Working up yields 2.9 g (76% of theory) of compound (100).

EXAMPLE 7

The procedure of Example 1 is repeated, using 0.0561 g 0.000025 mole) of palladium acetate, 50 ml of xylene, 7.63 g (0.025 mole) of stilbene-4,4'-dicarboxylic acid chloride, 2.60 g (0.025 mole) of ethyl acrylate and 3.38 g (0.025 mole) of N-benzyldimethylamine. Yield: 0.17 g of the compound of the formula

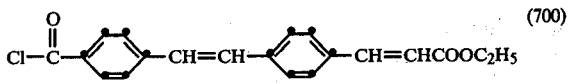
(700)

in the form of pale yellow crystals with a melting point of 143° C.

EXAMPLE 8

The procedure of Example 7 is repeated, using 1.33 g (0.025 mole) of acrylonitrile instead of ethyl acrylate. Working up yields the compound of the formula

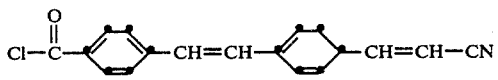

in the form of yellow crystals.

EXAMPLE 9

The procedure of Example 1 is repeated, using 0.0059 g (0.0000264 mole) of palladium acetate, 0.45 g (0.00132 mole) of the compound of the formula (700), 0.172 g (0.00165 mole) of styrene, 0.18 g (0.00132 mole) of N-benzyldimethylamine in 3 ml of p-xylene as solvent. Working up yields 0.09 g of the compound of the formula

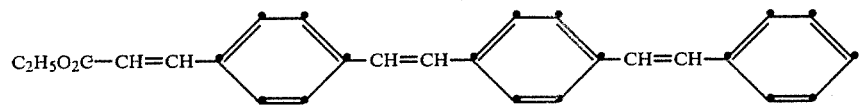

in the form of yellowish crystals.

EXAMPLE 10

Polyester fabric (Terylene ® 540) is padded at room temperature with a liquor which contains 1 g/l of the compound of the formula (701), (103), (104), or (111), and 1 ml of the condensation product of 8-9 moles of ethylene oxide and 1 mole of p-tert-octylphenol. The liquor pick-up is 80%. The fabric is then dried for 10 minutes at 80° C. and subsequently thermofixed at 200° C. for 30 seconds. A pronounced white effect is obtained on the treated fabric.

EXAMPLE 11

A polyester/cotton blend is treated in a dyeing machine, at a liquor ratio of 1:20, with an aqueous bath which contains 0.1%, based on the weight of the goods, of the compound of the formula (101), (103), (104), or (111), and 1 g/liter of the condensation product of 35 moles of ethylene oxide and 1 mole of stearyl alcohol. The bath is then heated from 40° to 97° C. in the course of 30 minutes, kept at this temperature for 30 minutes, and then cooled to 15° C. in the course of 15 minutes. The fabric is then rinsed in running deionised water and dried at 70° C. A pronounced white effect is obtained on the treated polyester/cotton blend.

What is claimed is:

1. A process for the production of a vinylstilbene compound of the formula

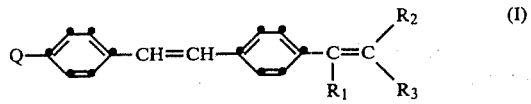

wherein Q is the grouping —COX or

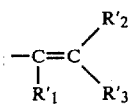

and wherein each of $R_1$ and $R_1'$ independently is hydrogen, cyano, alkyl or a non-chromophoric esterified carboxyl group, each of $R_2$ and $R_2'$ independently is hydrogen, alkyl or alkenyl each unsubstituted or substituted by non-chromophoric substituents, or is a non-chromophoric second order substituent, each of $R_3$ and $R_3'$ independently is hydrogen, cyano, or alkyl or alkenyl each unsubstituted or substituted by non-chromophoric substituents, and X is chlorine, bromine or iodine; or $R_1$ together with $R_3$ or $R_1'$ together with $R_3'$ are an alkylene bridge, with the proviso that not more than one of $R_2$ and $R_3$ and not more than one of $R_2'$ and $R_3'$ are hydrogen, and that, if Q is —COX, $R_1$ and $R_3$ are hydrogen and $R_2$ is carboxylic acid ($C_1$-$C_4$)alkyl ester or cyano, which process comprises reacting 1 molar equivalent of a compound of the formula II

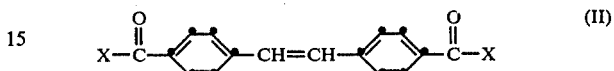

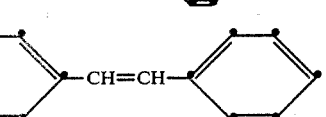

wherein X is as defined above, in the presence of a base and with the addition, as a catalyst, of palladium metal or a palladium compound which, under the reaction conditions, form labile palladium(O) compounds which do not contain phosphorus, with 1 molar equivalent of a compound of the formula III or with 1 molar equivalent of each of the compounds of the formulae III and IV

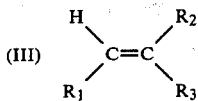 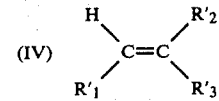

wherein $R_1$, $R_2$ and $R_3$ and $R_1'$, $R_2'$ and $R_3'$ are as defined above.

2. A process according to claim 1 which comprises the use of a compound of the formula II, wherein X is chlorine.

3. A process according to claim 1 for the production of a compound of the formula I, wherein Q is the grouping

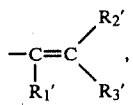

and wherein each of $R_1$ and $R_1'$ independently is hydrogen, cyano, $C_1$-$C_6$alkyl or —COOR''', each of $R_2$ and $R_2'$ independently is hydrogen or $C_1$-$C_6$alkyl unsubstituted or substituted by $C_1$-$C_4$alkoxy or $C_2$-$C_5$alkoxycarbonyl or is $C_2$-$C_4$alkenyl, —CN, —CF$_3$ or a group

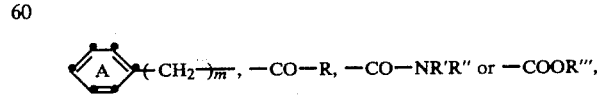

each of $R_3$ and $R_3'$ independently is hydrogen, cyano or $C_1$-$C_6$alkyl unsubstituted or substituted by $C_1$-$C_4$alkoxy or $C_2$-$C_5$alkoxycarbonyl, or $R_1$ and $R_3$ and $R_1'$ and $R_3'$ together are —(CH$_2$)$_3$ or —(CH$_2$)$_4$, with the proviso that not more than one of $R_2$ and $R_3$ and not more than one of $R_2'$ and $R_3'$ are hydrogen, R is methyl, $C_2$-$C_6$alkyl unsubstituted or substituted by $C_1$-$C_4$alkoxy or $C_4$-$C_6$alkoxyalkoxy, a radical of the formula

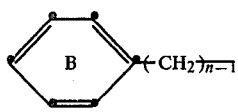

or naphthyl; R' is hydrogen, methyl, $C_2$-$C_6$alkyl unsubstituted or substituted by $C_1$-$C_4$alkoxy, $C_4$-$C_6$alkoxyalkoxy or di($C_1$-$C_4$-alkyl)amino, unsubstituted or methyl- or ethyl-substituted cyclohexyl or a radical of the formula

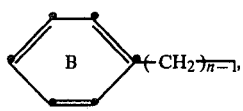

R" is hydrogen, methyl or $C_2$-$C_6$alkyl unsubstituted or substituted by $C_1$-$C_4$alkoxy or $C_4$-$C_6$alkoxyalkoxy; R''' is methyl, $C_2$-$C_6$alkyl unsubstituted or substituted by $C_1$-$C_4$alkoxy or $C_3$-$C_6$alkoxyalkoxy, unsubstituted or methyl- and/or ethyl-substituted cyclohexyl or a radical of the formula

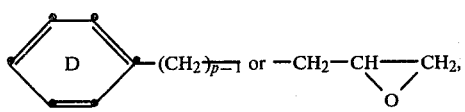

m is 1 or 2, each of n and p independently is 1, 2 or 3, whilst the rings A, B, C and D can be mono- or disubstituted by $C_1$-$C_3$alkyl and/or halogen, and, if each of n and p is 1, the aromatic rings B and D can be trisubstituted by $C_1$-$C_3$alkyl and/or halogen, or mono- or disubstituted by $C_1$-$C_3$alkoxy.

4. A process according to claim 3 for the production of a compound of the formula I, wherein Q is the grouping

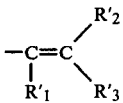

and wherein each of $R_1$ and $R_1'$ independently is hydrogen, —CN or $C_1$-$C_4$alkyl; each of $R_2$ and $R_2'$ independently is $C_2$-$C_4$alkenyl, —CN, —CONR'R", —COOR''' or —CO—R; and each of $R_3$ and $R_3'$ independently is hydrogen, —CN or $C_1$-$C_4$alkyl, whilst not more than one of $R_2$ and $R_3$ and not more than one of $R_2'$ and $R_3'$ are hydrogen; R is methyl, $C_2$-$C_6$alkyl unsubstituted or substituted by $C_1$-$C_4$alkoxy or $C_4$-$C_6$alkoxyalkoxy, or is naphthyl, or phenyl unsubstituted or substituted by halogen, $C_1$-$C_3$alkyl and/or $C_1$-$C_3$alkoxy; each of R' and R" is methyl; R''' is methyl or $C_2$-$C_6$alkyl unsubstituted or substituted by $C_1$-$C_4$alkoxy or $C_3$-$C_6$alkoxyalkoxy; m is 1, each of n and p independently is 2 and, in particular, 1.

5. A process according to claim 3 for the production of a compound of the formula I, wherein Q is the grouping

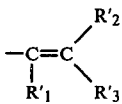

and wherein each of $R_1$ and $R_1'$ and $R_3$ and $R_3'$ is hydrogen, —CN or $C_1$-$C_4$alkyl, each of $R_2$ and $R_2'$ is $C_2$-$C_4$alkenyl, —CN, —CONR'R", —COOR''' or —CO—R, whilst not more than one of $R_2$ and $R_3$ and not more than one of $R_2'$ and $R_3'$ are hydrogen, R is $C_1$-$C_6$alkyl or phenyl unsubstituted or substituted by halogen, $C_1$-$C_3$alkyl or $C_1$-$C_3$alkoxy, in particular unsubstituted $C_1$-$C_4$alkyl or phenyl unsubstituted or monosubstituted by chlorine, methyl or methoxy; each of R' and R" is methyl and R''' is methyl or $C_2$-$C_6$alkyl unsubstituted or substituted by $C_1$-$C_4$alkoxy or $C_3$-$C_6$alkoxyalkoxy, especially unsubstituted $C_1$-$C_4$alkyl.

6. A process according to claim 3 for the production of a compound of the formula I, wherein Q is the grouping

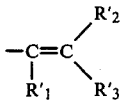

and wherein each of $R_1$ and $R_1'$ is methyl and preferably each is hydrogen, each of $R_2$ and $R_2'$ is —CN or —COOR''', R''' is unsubstituted $C_1$-$C_4$alkyl and each of $R_3$ and $R_3'$ is methyl or ethyl and preferably hydrogen.

7. A process according to claim 1 for the production of a compound of the formula I, wherein Q is —COCl, $R_1$ and $R_3$ are hydrogen, and $R_2$ is carboxylic acid ($C_1$-$C_4$)alkyl ester or cyano.

8. A process according to claim 1, wherein the palladium compound is $PdCl_2$, palladium acetylacetonate and, palladium acetate.

9. A process according to claim 1, wherein the reaction is carried out in the temperature range from 0° to 200° C., in particular from 90° to 150° C., and in the presence of an organic solvent which is inert to the reaction components.

10. A process according to claim 9, wherein the solvent is anisole, xylene or toluene.

11. A process according to claim 1, wherein the base is a trialkylamine containing 4 to 12 carbon atoms in each of the alkyl moieties.

12. A process according to claim 1, wherein 0.0001 to 20 mol.% of catalyst is used, based on the compound of formula III.

13. The process of claim 8, wherein the palladium compound is palladium acetate.

* * * * *